(12) United States Patent
Asgari

(10) Patent No.: US 9,969,966 B2
(45) Date of Patent: May 15, 2018

(54) BIOREACTOR SYSTEM FOR CONTINUOUS CELL CULTIVATION

(75) Inventor: Sohéil Asgari, Wiesbaden (DE)

(73) Assignee: ATECH PARTNERS LIMITED, Wiesbaden (DE)

( * ) Notice: Subject to any disclaimer, the term of this patent is extended or adjusted under 35 U.S.C. 154(b) by 386 days.

(21) Appl. No.: 14/118,979

(22) PCT Filed: May 30, 2011

(86) PCT No.: PCT/EP2011/002663
§ 371 (c)(1),
(2), (4) Date: Nov. 20, 2013

(87) PCT Pub. No.: WO2012/163368
PCT Pub. Date: Dec. 6, 2012

(65) Prior Publication Data
US 2014/0080212 A1  Mar. 20, 2014

(51) Int. Cl.
*C12M 1/12* (2006.01)
*C12M 1/00* (2006.01)
*C12M 3/00* (2006.01)
*C12M 1/26* (2006.01)

(52) U.S. Cl.
CPC ............ *C12M 25/02* (2013.01); *C12M 21/08* (2013.01); *C12M 23/34* (2013.01); *C12M 25/14* (2013.01); *C12M 29/10* (2013.01); *C12M 33/04* (2013.01)

(58) Field of Classification Search
None
See application file for complete search history.

(56) References Cited

U.S. PATENT DOCUMENTS

| 6,303,375 | B1 | 10/2001 | Kimura et al. |
| 2008/0311650 | A1 | 12/2008 | Jakob et al. |
| 2011/0212493 | A1* | 9/2011 | Hirschel ............... C12M 23/28 435/91.4 |
| 2011/0223581 | A1 | 9/2011 | Stobbe |
| 2011/0236932 | A1 | 9/2011 | Stobbe |
| 2011/0263021 | A1 | 10/2011 | Stobbe |

FOREIGN PATENT DOCUMENTS

| EP | 0 967 273 | 12/1999 |
| WO | 2005/108550 | 11/2005 |
| WO | 2010/048417 | 4/2010 |
| WO | 2010/069319 | 6/2010 |

OTHER PUBLICATIONS

Wendt, D., et al: Oscillating Perfusion of Cell Suspensions . . . Biotechnology and Bioengeneering, Wiley & Sons, Hoboken, NJ, US, vol. 84, No. 2, Oct. 20, 2003, pp. 205-214 (In English).

* cited by examiner

*Primary Examiner* — Blaine Lankford
(74) *Attorney, Agent, or Firm* — Collard & Roe, P.C.

(57) ABSTRACT

A cell culture system for fermentation or cultivation of at least one of cells, tissues or tissue-like cell cultures, organs or organ-like cell cultures and multicellular organisms comprises:
- a system vessel (1) in which at least one cavity (6) is formed, the cavity (6) having at least three ports (2, 3, 4);
- at least one porous substrate (9) installed within the cavity (6) so as to allow fluid flowing from any one to any other of said three ports (2, 3, 4) to pass through said porous substrate (9); and,
- at least one channel extending from a first one of said ports (3) within the porous substrate (9) towards a central region of said porous substrate (9).

20 Claims, 4 Drawing Sheets

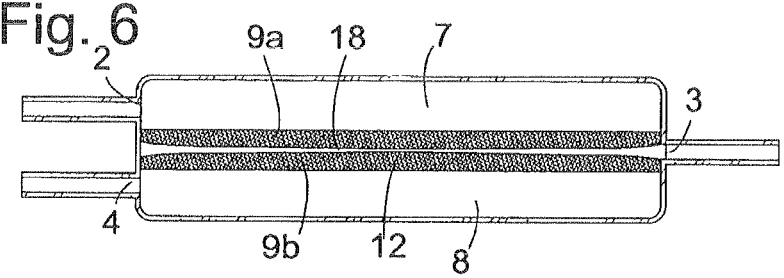
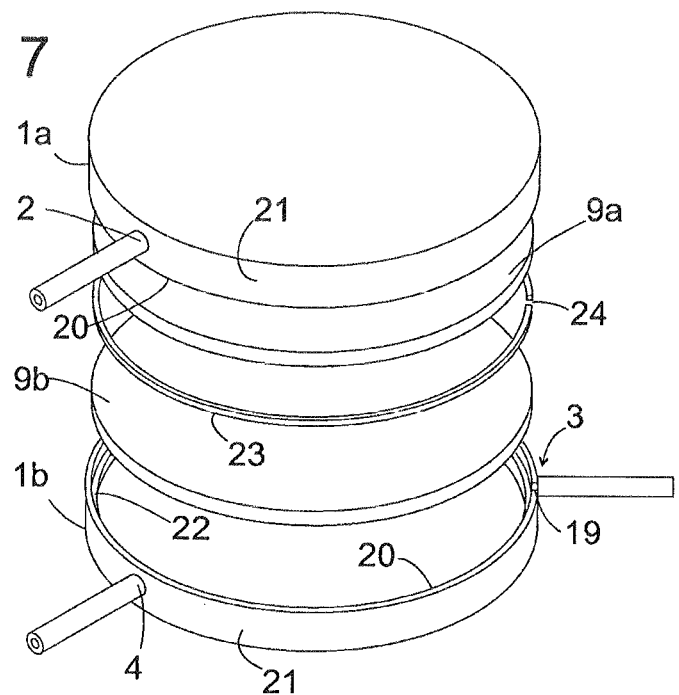
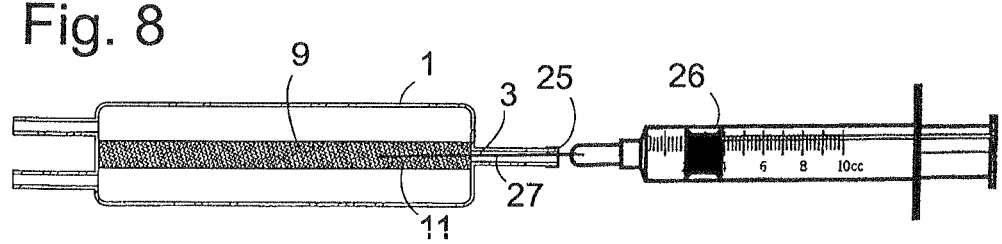

BIOREACTOR SYSTEM FOR CONTINUOUS CELL CULTIVATION

CROSS REFERENCE TO RELATED APPLICATIONS

This application is the National Stage of PCT/EP2011/002663 filed on May 30, 2011, the disclosures of which are incorporated by reference. The international application under PCT article 21(2) was not published in English.

FIELD OF THE PRESENT INVENTION

The present invention relates to new cell culture systems. Throughout the following description the term "cell culture" or "cell cultivation" shall be understood broadly, referring to the cultivation not only of unicellular organisms but also of tissues or tissue-like cell cultures, organs or organ-like cell cultures derived from multicellular organisms, fermentation processes and the like in industrial or medical or pharmaceutical applications.

BACKGROUND INFORMATION

Cell cultivation systems are widely used for cultivation and expansion of cell cultures and production of biological compounds. Main applications are growing and expansion of cells, tissue, manufacturing of cellular products and virus particles for purposes like e.g. production of diagnostic or therapeutic biopharmaceuticals. Fermentation is widely used for production of food additives like, but not limited to, vitamins, amino acids, citric acid, acetic acid, arabic gum, xanthan gum, monosodium glutamate, and the like; as well as aroma molecules, biodegradable plastics like polyhydroxibutyrate or biopolymers, pigments, dyes, insecticides, and the like.

Mostly, industrial-scale cell cultivation processes are carried out in cell suspensions. While cell cultivation in suspension is usually not critical for bacteria or yeasts, mammalian cell cultivation in suspension is more demanding. Typically, suspension-based cell cultivation processes are carried out in stirred tanks or, recently getting more and more used, in reactors that shake or rotate culture vessels. However, suspension cultivation is prone to shear stress and poor mass transfer; additionally, a comparably low ratio of biomass versus used liquid cell culture medium is provided. Most of commercially relevant mammalian cell cultures are derived from adherently growing mammalian cell cultures that must be adapted to suspension growth beforehand; especially primary cells, e.g. adipose-tissue derived stem cells, are more difficult to adapt or even not adaptable to suspension.

Adaptation is a time-consuming process that requires up to several years and may delay the development of robust large-scale manufacturing processes. Moreover, adaptation often requires the use of animal-derived serum and other supplements to be added to the cell culture medium in order to facilitate or even enable the adaptation to suspension cultivation. Animal-derived compounds may comprise harmful impurities that may cause allergic reactions or infectious diseases from the source animals.

Another well-known drawback of adaptation is the loss of productivity of such-like cell cultures that usually produce significantly less protein, i.e. the cell product or cell byproduct, when adapted to and staying in suspension compared to non-adapted adherent growth. When using cell lines, so called "high producers", i.e. clones with high specific productivity for expressed cell products, may turn into "low producers" after adaptation to suspension.

As an alternative approach, cells may be grown adhering to a substrate in special cell culture or bioreactor systems. General advantages of adherent cultivation are both the high ratio of biomass versus used liquid cell culture medium in the cultivation system and significantly higher productivities of the cell cultures regarding cell products and by-products. Moreover, the use of animal-derived serum is principally expendable thus avoiding potential harmful impurities in the cell culture and cell culture products. Eliminating the need of adaptation also results in a significant reduction of the time that is needed to develop the aforesaid robust manufacturing process saving up to several years.

However, adherent cell cultivation comprises significant drawbacks in scaling up the process technically, because standard cell cultivation systems provide a limited surface area for the adherent growth of cell cultures. The cultivation process is limited rather by the available effective surface area in the cultivation system than by the cell concentration in the cell culture medium. Cell culture systems that are specifically designed for adherent cell cultivation, e.g. T-flasks, roller bottles, cell stacks and the like, comprise simple two-dimensional surfaces for attaching and expanding the cell culture. Biologically, adherently growing cell cultures require initially a minimum number of cells per surface area to be seeded, i.e. the number of cells needed for successfully seeding a substrate is proportional to the surface of the substrate. Further, there is a maximum cell density on the substrate that cannot be exceeded. In consequence, starting with a small number of cells, it is not possible to seed a large culture system straight away, and if a small culture system is seeded, the number of cells that can be grown in it is limited. Accordingly, in order to obtain the numbers of cells needed for large-scale production, the cells must first be cultivated in a small culture system, and when the maximum cell density has been reached in this system, the cell culture must be passaged by detaching the cells chemically and/or mechanically, and re-seeded on a larger substrate surface in one or more cultivation systems at the required minimum cell density. Hence, expansion and growth of the culture on large scale processing requires a continuous passaging with detaching and again seeding the culture into additional cultivation systems. Scaling up this kind of processes requires a comparatively large number of operational steps, labor and space, i.e. footprint, for handling and incubating the cultivation systems.

Existing approaches in cultivation systems for adherent cell cultivation are based on enhancement of available growth surface either by specific design of the cultivation vessel and/or using carriers or other fillers like structured packings and the like. Known carriers that increase the surface for adherent cell growth are micro- or macrocarriers ("substrates"), i.e. spherical particles, usually made out of cellulose, dextrane, gelatine, polystyrol, alginate, glass, carbon, ceramics or other organic, preferably polymeric materials, and the like, either chemically or biologically modified (or not). Commercially available substrates can include, for example, Cytodex®, Cytopore®, Cultisphere®, Microhex® and the like. Usually, such substrates are used in stirred tanks, roller-bottles or spinner systems. In some applications such-like substrates are used in fluidized bed reactors.

Advanced solutions focus on optimizing the usage of provided surface area by optimizing nutritional conditions and gas exchange. E.g., US 2008206734 describes a cultivation system that is based on enlarging the surface area and aims to improve the nutritional conditions and overall efficiency of the system by controlling the convection of liquid cell culture medium and gas exchange.

Nevertheless, all approaches that are based on increasing the available surface area or surface area/volume ratio of the given cultivation system require a significantly increased total, i.e. absolute, number of cells for initial seeding and starting the cell cultivation process. Consequently, an increase of surface area results in an increase of required absolute cell numbers for inoculation into the bioreactor system and this may only be achieved by producing according cell numbers in smaller systems previously. Passaging, i.e. detaching and seeding, may even require more separate cell culture systems before one may use the advanced systems with high surface areas. For example, cultivation in a system that comprises a tenfold increase of available surface area compared to another cultivation system cannot be started with the same absolute number of cells in the seeding suspension, but with the tenfold higher absolute cell number. The benefit of high surface cultivation systems may only be reducing the number of parallel cultivation systems at large scale production, but is not useful to avoid passaging from cultivation vessel to cultivation vessel.

In particular, the use of suspended particulate substrates requires very complicated procedures of inoculation with fractional increase of cell culture medium and different steps of adjusting the agitation (e.g. stirring). Cell attachment on suspended particulate substrates is a random process resulting in a patchy distribution on the substrates' surfaces. Moreover, expansion and growth of cell cultures is depending on transfer from substrate particle to particle while agitation (e.g. stirring) of the cell culture medium induces collision between substrate particles and causes shear and mechanical damages to the cell culture. Medium exchange during the cultivation process is as complicated as inoculation requiring a separation of suspended particulate substrates and sometimes passaging by introducing an additional amount of suspended particulate substrates and reseeding of detached cells. Using fluidized bed reactors also is prone to suboptimal inoculation with patchy distribution, insufficient convection of medium with uneven distribution of medium flow and formation of dead areas as well as mechanically instable packed beds that are sensitive to high flow-rates of cell culture medium and according swirling of the substrate particles. Additional general constraints for using substrates are related to, but not limited to, the formation of by-products from organic substrates, that may occur as impurities in the manufacturing product, or absorption of the valuable biological compound. Yield and purification is then getting a complicated and costly downstream process.

It would be a significant improvement if cell cultivation for industrial or medical or pharmaceutical applications could be performed with combining the advantages of suspension cultivation with those of adherent cell cultivation in order to reduce direct and indirect costs, the time of development cycles and time to market for new cell culture products and respective manufacturing processes. As well, it would be beneficial to eliminate the drawbacks of both cultivation principles, i.e. the demand for excessive stirring and convection in suspension systems as well as the limitations by surface area and the need for passaging in adherent systems. Moreover, it would be beneficial to eliminate mechanical parts from inside the cultivation system (e.g. stirrers), shear on the cell culture and to simplify inoculation, growth and expansion of the cell culture process at all.

The object of the present invention is to provide a cell culture system and a method of operation thereof, which are easy to use and facilitate the growth of homogenous, productive cell cultures. Particularly, one exemplary object of the present invention is to provide a system and process for adherent or semi-adherent cell cultivation without the need of passaging at expansion and growth phase of the culture.

The object of the invention is achieved, on the one hand, by a cell culture system comprising
(i) a system vessel in which at least one cavity is formed, the cavity having at least three ports;
(ii) at least one porous substrate installed within the cavity so as to allow fluid flowing from any one to any other of said three ports to pass through said porous substrate;
(iii) a channel extending within the porous substrate from a first one of said ports towards an inner region of the porous substrate.

If cells to be cultivated are introduced into the porous substrate by said channel, e.g. when injected in the form of a liquid inoculum with the inoculum being spread through the pores of the substrate by capillary action, they can be placed directly in the inner region of the substrate, from where they can easily spread all over the substrate by cell growth.

The porous substrate may fill a cavity of the system vessel completely. In a preferred embodiment, however, the porous substrate forms a partition between upstream and downstream portions of said cavity, a second one of the ports being connected to the upstream portion, and a third one of the ports being connected to the downstream portion. When e.g. a culture medium is supplied through the second port and discharged through the third port, the upstream and downstream cavity portions help to distribute the flow of the culture medium homogenously all over the substrate, so that equally favorable conditions for growth are achieved throughout the substrate.

The porous substrate may have a cubic, discoid, tubular or cylindrical geometry.

The porous substrate may have edges in sealing contact with the walls of the cavity, so that any flow between said second and third ports must pass through the porous substrate.

Preferably, the porous substrate is a solid body formed e.g. by sintering a particulate material, such as glass, ceramic or plastic powder.

In a tube-shaped porous substrate, one of the upstream and downstream portions may extend within the tube, whereas the other extends around the tube. In this way, a large volume of porous substrate can be accommodated in a compact system vessel while maintaining highly homogenous growth conditions all over the porous substrate.

The channel may be a recess formed in said porous substrate. An inoculum injected into the channel can advance freely in it towards the inner region of the substrate, so that the cell concentration needed for a successful seeding will be reached in the inner region, and, from there, the cells will subsequently spread into the substrate in all directions. Thus the cells can spread quickly all over the substrate, and higher growth rates can be achieved than by seeding at the periphery of the substrate.

The channel may also be a gap between two parts of said porous substrate. The gap may have a predetermined, non-zero width defined e.g. by spacers installed between said two parts of the porous substrate. However, even a gap of practically zero width between two parts of the porous substrate that are in direct contact with each other will facilitate the spreading of inoculum throughout the porous substrate.

According to a further alternative, the channel may be a tube extending into the substrate. While in a recess, seeding may occur anywhere at the surface of the recess, the tube releases the inoculum only at its end, ensuring that seeding will occur only in the inner region of the substrate.

The porosity of the substrate should be such as to allow efficient spreading of the inoculation liquid by capillary action, i.e. sizes and surface properties of the porous substrate should be such as to allow water to rise within the porous substrate by capillary force.

If the substrate has pores of widely varying sizes, the flow of a culture medium will be strongest wherever large pores combine to form a path through the substrate, whereas in small pores, the flow may be very slow or even stagnant.

Cell growth may be limited due to lack of nutrients in small pores, and due to excessive shear stress caused by a strong flow of culture medium in large pores. Homogenously sized pores greatly facilitate efficient cell growth. Therefore, a fraction of at least 50%, preferably at least 60%, more preferred at least 75% of the total pore volume of the porous substrate should be formed by pores the size of which differs by a factor of not more than 2.

The minimum pore size of the above-mentioned fraction may be 10 µm (in that case, the pores of said fraction should have sizes from 10 µm to not more than 20 µm), and the maximum pore size should be 500 µm (in that case, the fraction should have pore sizes from at least 250 µm to 500 µm). A porous substrate that fulfills these requirements can be produced e.g. by sintering a granular material having a sufficiently homogenous grain size.

Porosity of the porous substrate should be high, so that a large quantity of cells can be grown in the pores. On the other hand, if the porosity is too high, the surface area on which the cells may adhere becomes insufficient. Therefore, for optimum growth, porosity of substrate should be in a range from 15% up to 90%, preferably from 20% to 80%, more preferred from 25 to 75% and most preferred from 25% to 60%.

The porous substrate should be fixed to a wall of the cavity, preferably by welding or gluing or using spacer elements. Welding or gluing is particularly appropriate in case of a disposable system vessel, whereas in a system vessel for multiple uses, spacers are more adequate for removably fixing the porous substrate.

In addition to the first to third ports mentioned above, one or more additional ports may be provided for insertion of probes or sensors. Such probes or sensors may be temporarily installed, e.g. plugged into an opening of the port, or they may be permanently installed, e.g. by fusing.

The object of the invention is further achieved by a method of operating the cell culture system defined above, the method comprising the steps of
a) introducing cells to be cultivated into the porous substrate by said channel,
b) feeding a culture medium by a second one of said ports,
c) discharging the culture medium by a third one of said ports.

Since the cells to be cultivated can be introduced through the first port and the channel while there is no flow of culture medium, they can attach to the surface of the porous substrate without a risk of being washed away by the culture medium. The feeding of culture medium can be delayed until a sufficient amount of the introduced cells has adhered to the porous substrate.

The size of the region of the substrate which is effectively seeded with cells can be controlled based on the volume of inoculum used for seeding: The smaller this amount is, the smaller is the region of the substrate in which the inoculum spreads and in which, in consequence, the injected cells can adhere to the substrate. If it is desired to seed only part of the substrate, the volume of inoculum used should be less than the total pore volume of the substrate. Thus, in a cell culture system of the present invention, a large substrate can be successfully seeded with a small number of cells if these cells are initially confined to a small region of the substrate by using a small volume of inoculum.

On the other hand, the concentration of the cells in the inoculum should be adapted to the porosity characteristics, in particular to the volume/surface ratio of the pores of the substrate, so that if a pore is filled with inoculum, the number of cells in the pore is such that when the cells adhere to the surface of the pore, the minimum cell density necessary for further growth is reached.

Inoculation may be performed in one step by injecting a defined volume of cell suspension with a defined cell concentration through the first port and channel. If suitable, inoculation may be performed in multiple steps by injecting further volumes of cell suspension to increase the number of cells per wetted surface area. The porous substrate may be dry when injecting the inoculum or pre-wetted with physiologic or cell culture medium. As known in the art, the cell culture and respective cells will attach to the substrate surface depending on inherent cell culture properties and environmental factors. Cell attachment may take a few minutes up to several hours. The number of attached cells may be significantly increased by additional and fractionated injections over several hours or days.

Further features and advantages of the invention will become apparent from the subsequent description of embodiments thereof referring to the appended drawings.

FIG. 6 is a cross section according to a fourth variant;

FIG. 7 is an exploded view of the fourth variant;

FIG. 8 illustrates the inoculation process according to a fifth variant of the first embodiment;

Figure 1:
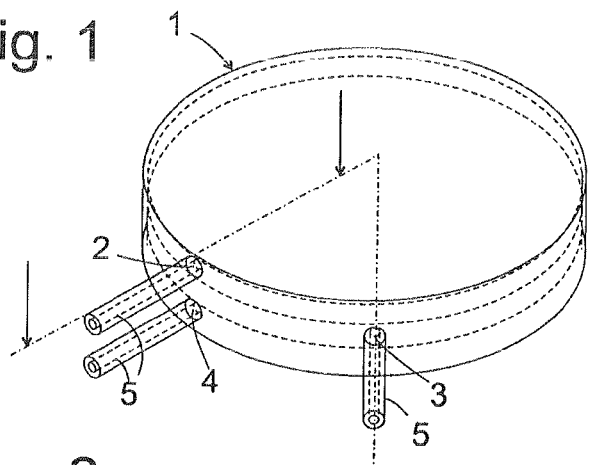
FIG. 1 is a perspective view of a cell culture vessel according to a first embodiment of the invention.

FIG. 1 is a perspective view of a cell culture system according to a first embodiment of the invention. It comprises a vessel 1 in the shape of a disk or a short cylinder. The vessel 1 can be made of any material that is appropriate for cell cultivation, such as stainless steel, a polymer or glass, e.g. borosilicate glass, or any combination thereof. Three ports 2, 3, 4 are formed in a circumferential wall of vessel 1. At the ports 2, 3, 4, short tubular projections 5 are formed which extend radially from the vessel circumferential wall and to which tubes or hoses for introducing inoculum, supplying and draining culture medium can be connected. In FIG. 1, the projections 5 of ports 2, 4 extend in a same radial plane, so that in the cross section of FIG. 2, all three ports 2, 3, 4 can be shown. In practice, the projections 5 of the three ports will usually extend in different directions.

A cavity 6 formed inside cell culture vessel 1 is divided into first and second spaces 7, 8 by a porous substrate 9. The porous substrate 9 is shaped as a circular disk, a circumferential edge 10 of which is in intimate contact with the circumferential wall of vessel 1, so that a culture fluid which is supplied e.g. through port 2 to space 7 can reach second space 8 only by passing through the pores of substrate 9.

The substrate 9 has a recess 11, the outer end of which is formed at the circumferential edge 10 and communicates with port 3, and which extends radially towards the geometrical center 12 of substrate 9. The substrate 9 may be formed from any material that is suitable as a support for cell cultivation, preferably from polycarbonate, carbon, ceramic or glass, particularly borosilicate glass. Preferably, the porous substrate 9 is formed by sintering grains of the substrate material, since if grains of substantially homogenous size are used, pores having substantially the same size can be obtained all over the substrate 9, ensuring equally favorable conditions for cell growth throughout the substrate 9.

The culture vessel 1 of FIG. 1, 2 may be operated as follows: initially, the spaces 7, 8 are filled with air, and the substrate 9 is dry or slightly moist, its pores being substantially filled with air, too. An inoculum containing cells to be cultivated is introduced through port 3 and can flow freely towards the center 12 of substrate 9 through recess 11. The average pore size of substrate 9 should be at least twice, preferably at least three times the average size of the injected cells, so that these can propagate freely through the pores of substrate 9 without being trapped in the vicinity of recess 11 by a filtering effect of the substrate 9. By applying a volume of inoculum which is smaller than the volume of the pores of the substrate 9, it can be ensured that those pores which the inoculum does not fill are not seeded, i.e. seeding is confined to an inner region of the substrate 9 in which the inoculum has spread. The system may now be left to rest for some time, so that the cells may settle and adhere to the substrate 9. The duration of this phase depends on the type of cells to be cultivated and environmental conditions. When the cells can be expected to have adhered in a sufficient amount, the process may be repeated in order to reach the necessary minimum or even higher cell concentrations for further growth in the inoculated region. Subsequently, culture medium is supplied through port 2, so that it may spread on the horizontal upper surface of substrate 9, pass through it into space 8 and be evacuated from there through port 4.

Figure 2:
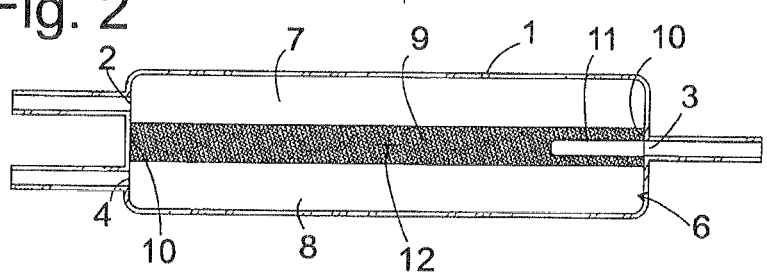
FIG. 2 is a cross section of the cell culture vessel of FIG. 1.
Figure 3:
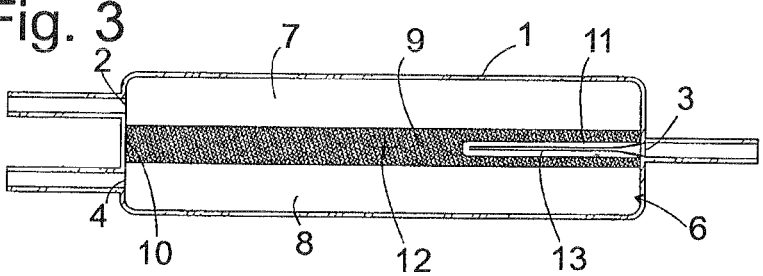
FIG. 3 is a cross section analogous to FIG. 2 according to a first variant of the first embodiment.

The variant of FIG. 3 is different from that of FIG. 2 by a capillary tube 13 that extends from port 3 towards the inner end of recess 11. By injecting the inoculum through tube 13, it can be ensured that the inoculated region is at the inner end of recess 11, far away from the periphery of substrate 9. From there, the cells may grow into all directions, at least initially unimpeded by peripheral surfaces of the substrate 9, so that the time the cells need to spread all over the substrate 9 by growth is short.

Figure 4:
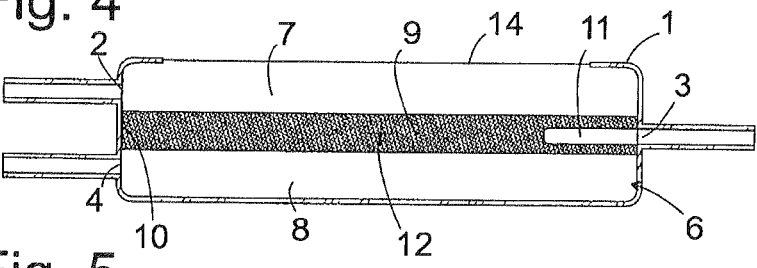
FIG. 4 is a cross section of a second variant of the first embodiment.

The variant of FIG. 4 differs from that of FIG. 2 by the design of the culture vessel 1. While according to the previously discussed variants the culture vessel 1 had a homogenous, impermeable wall formed e.g. of glass, plastic, steel or the like, in the variant of FIG. 2 part of the vessel wall enclosing first space 7 is replaced by a gas-permeable diaphragm 14. Such a diaphragm 14, while being impermeable to cells or viruses, may allow atmospheric oxygen to enter space 7 and become dissolved in the culture medium circulating in it, thus providing a convenient means for supplying oxygen or any other gas that may be needed for culture of the in substrate 9.

Figure 5:
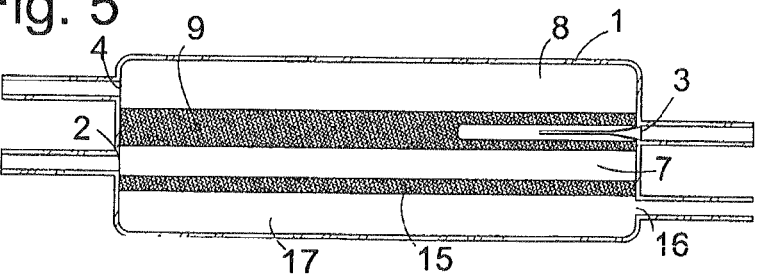
FIG. 5 is a cross section according to a third variant.

In the variant of FIG. 5 a porous body 15 may be regarded as part of a wall of a cell culture cavity comprising first and second spaces 7, 8 and substrate 9. By a fourth port 16 connected to a chamber 17 formed underneath porous body 15, a gas such as air or oxygen can be supplied. After passing through porous body 15, the gas will form finely dispersed bubbles in a culture medium supplied to first space 7 by port 2, so that a culture medium rich in dissolved gas will pass through substrate 9.

Composition and structure of porous body 15 may be the same as that of substrate 9.

In the embodiment of FIG. 6, porous substrate 9 comprises two distinct porous bodies 9a, 9b, and port 3 communicates with a narrow gap 18 between said porous bodies 9a, 9b. The gap 18 is so narrow that when inoculum is supplied through port 3, it is immediately attracted by capillary action into the gap 18. Facing sides of the porous bodies 9a, 9b are slightly convex, so that the capillary action draws the inoculum to the center 12 of the substrate. From there, it penetrates into the porous bodies 9a, 9b, so that the cells contained in the inoculum will settle in an inner region of the substrate at either side of center 12.

FIG. 7 is an exploded view of the cell culture system of FIG. 6, showing the components from which it is formed. It should be noted, though, that the variants of FIGS. 1 to 5 are formed substantially according to the same principle. The cell culture vessel 1 is comprises two shells 1a, 1b, each having substantially the shape of a Petri dish and having a port 2, 4, respectively, formed in its circumferential wall. Port 3 is here formed by two cutouts 19 in facing edges 20 of shells 1a, 1b. According to a variant not shown in the figures, port 3 might be formed in a ring having the same diameter as the shells 1a, 1b and installed between the facing edges 20 of these.

At an inner side of the circumferential walls 21 of shells 1a, 1b, there is formed a step 22 on which the porous substrate 9, or incidentally, one of the porous bodies 9a, 9b forming substrate 9, can be placed. A spacer ring 23 is provided for defining the width of the gap 18 between porous bodies 9a, 9b. The spacer ring 23 has a cutout 24 facing port 3, in order not to obstruct the introduction of inoculum therethrough.

Obviously, such a step 22 can be provided in the variants of FIGS. 2 to 5, too, in order to define the position of installation of substrate 9.

In the embodiment of FIG. 8, at the time of manufacture of the cell culture system the porous substrate 9 has no recess. Port 3 of vessel 1 is sealed by a rubber membrane 25. The inoculum is introduced using a syringe 26. The injection needle 27 of the syringe 26 penetrates the rubber membrane 25 and the porous substrate 9. The recess 11 is thus formed by the injection needle 27 at the time of inoculation. If the porous substrate 9 is elastic, the recess 11 may close again once the needle 27 is withdrawn, just like, the injection opening in rubber membrane 25.

Figure 9:
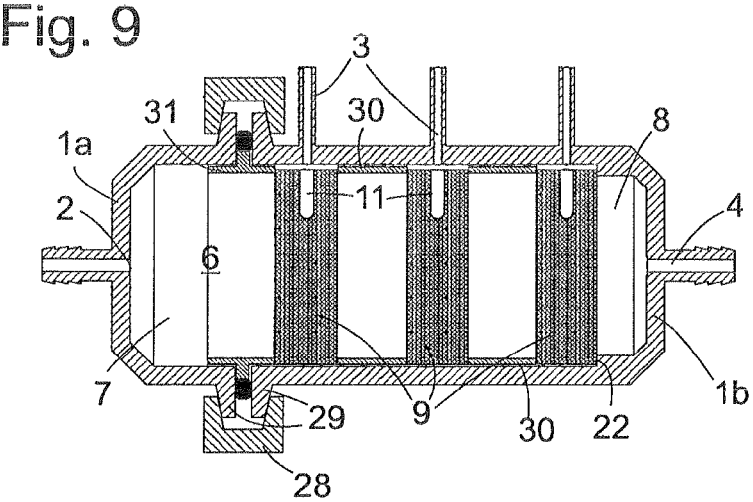
FIG. 9 is a longitudinal section of a cell culture vessel according to a second embodiment.

FIG. 9 is an axial cross section of a culture vessel 1 according to a second embodiment of the invention. The culture vessel 1 is again formed of two shells 1a, 1b. These are held in sealing contact by an annular clamp 28 extending around facing flanges 29 of the shells 1a, 1b. The clamp 28 and flanges 29 may be e.g. of the KF type known in vacuum technology.

In FIG. 9 three porous substrates 9 having a recess 11 facing a port 3 are installed along the axis of culture vessel 1, so that a culture medium flowing through the vessel 1 from port 2 to port 4 will pass through one of the substrates 9 after the other. The positions of the substrates 9 are defined by a step 22 of shell 1b, spacer rings 30 and a conventional KF support ring 31 which radially supports an O-ring in a gap between flanges 29. If the clamp 28 is removed, the shells 1a, 1b can be taken apart, and the substrates 9 and spacer rings 30 can be removed. If it is desired to reduce further the growth and expansion time of the cultivation, i.e. the time in which the cell culture spreads over the complete surface of substrates 9, it may be beneficial to perform inoculation of several substrates 9 by their respective ports 3 at the same time.

If desired, the spacer rings 30 might be replaced by porous substrates which, not being connected to a port 3, cannot be inoculated directly, but which can be populated by cells spreading into them from an inoculated substrate 9.

If the supply of starter cells is limited, it is sufficient to inoculate just one of the multiple substrates 9 and let the cells spread from one substrate 9 to the next.

Figure 10:
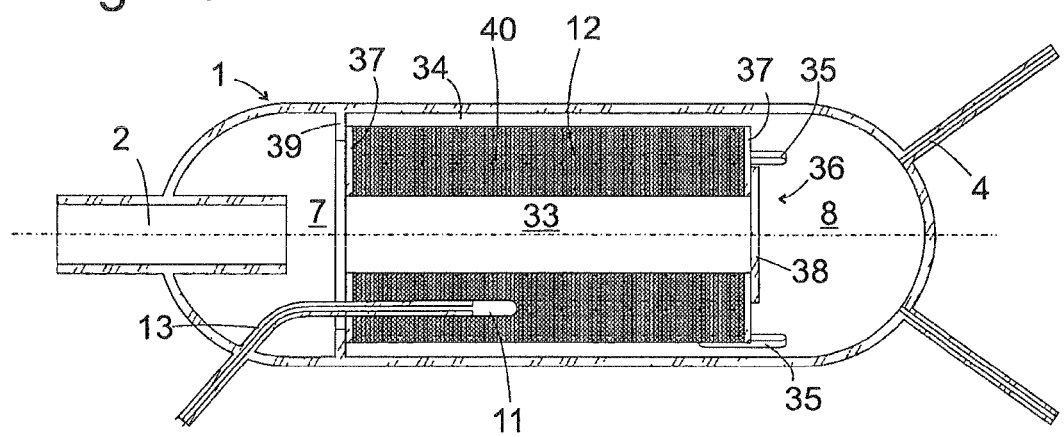
FIG. 10 is a longitudinal section of a cell culture vessel according to a third embodiment.

FIG. 10 is a longitudinal section of a culture vessel 1 according to a third embodiment of the invention. Like the vessel of FIG. 9, it is generally in the shape of an elongate cylinder having ports 2, 4 for the inflow and outflow of a culture medium at its ends. The porous substrate 9 is shaped as a thick-walled cylindrical tube. The tube is installed within vessel 1 so as to form a partition between first space 7 comprising an internal cavity 33 of the tube, and second space 8, a part 34 of which extends around the tubular substrate. The tubular substrate 9 has its longitudinal axis aligned with the axis of vessel 1, e.g. by spacer webs 35 extending from an inner side of the wall of vessel 1 towards the substrate 9, so that the width of space 34 is constant both in the axial and circumferential directions.

An impermeable cover 36 is fixed to a face side of substrate 9, separating internal cavity 33 from space 8. The cover 36 might be formed in one piece from a circular disk of impermeable material having the same diameter as substrate 9. In the embodiment of FIG. 10, the cover 36 comprises an annular impermeable layer 37 formed by superficially melting the particles of substrate 9, and a platelet 38 extending across internal cavity 33.

At the other face side of substrate 9, a second impermeable layer 37 is formed. The presence of the impermeable layers and the tubular shape of substrate 9 ensures a perfectly radial flow of culture medium through substrate 9 and highly homogenous conditions for cell growth along the entire length and over the complete circumference of tubular substrate 9.

The substrate 9 is held in place by the second impermeable layer 37 being fused or glued to an angular web 39 that protrudes inwardly from the wall of vessel 1.

The tubular substrate 9 cannot be inoculated at its geometrical center 12, since it is also the center of internal cavity 33. Instead, a recess 11 is formed within the tubular body of substrate 9 extending from a front side thereof in its axial direction, and a capillary tube 13 extends from port 3 through space 7 and into recess 11. In this way inoculum can be applied directly to a region of substrate 9 which, although not being in the geometrical center of substrate 9, can be regarded as an inner region due to the fact that from there the cells can spread into all regions of the substrate 9 by short paths and can thus populate the entire substrate 9 in a short time.

In the embodiment of FIG. 10, the length of the tubular porous substrate 9 is about twice its diameter, so that a path by which cells can spread from the inoculated region at the end of recess 11 to the side faces of substrate 9 is about as long as a path by which they will spread in the circumferential direction, around internal cavity 33, to a point 40 opposite recess 11. Therefore, the substrate 9 can be expected to be homogenously populated in a short time.

Figure 11:
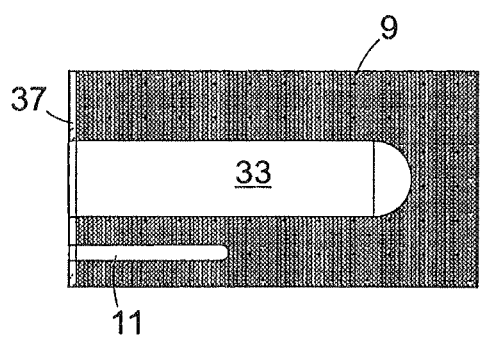
FIG. 11 illustrates a variant of a porous substrate for the culture vessel of FIG. 11.

FIG. 11 is an axial section of the porous substrate for use in the vessel 1 of FIG. 10 according to a variant of the invention. Here the internal cavity 33 is formed as a blind hole, and an impermeable layer 37 is provided only at one face side of substrate 9. According to this variant, the flow of culture medium may be distributed not quite as evenly throughout the substrate as in the embodiment of FIG. 11, but the total volume of pores in which cells can be cultivated is larger.

Figure 12:
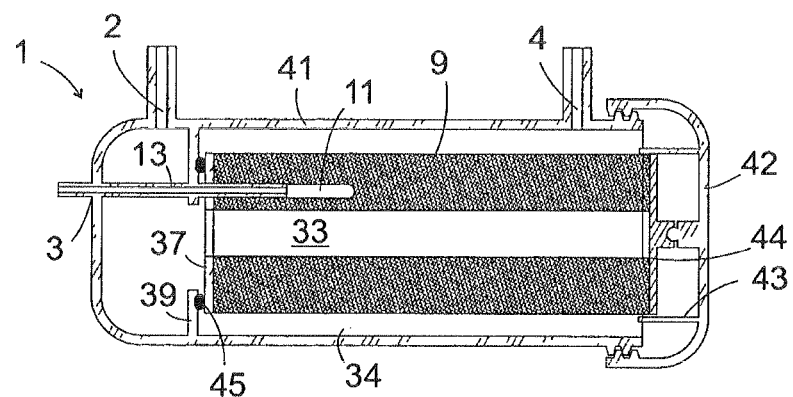
FIG. 12 is a longitudinal section according to a fourth embodiment of the invention.

FIG. 12 is another embodiment of a culture system in which the porous substrate is tubular, and the vessel 1 can easily be opened in order to replace the substrate 9. The culture vessel 1 comprises an elongate cylindrical can 41 having ports 2, 4 for introduction and removal of culture fluid formed in a circumferential wall, and port 3 for inoculation at a first face side thereof. The second face side of can 41 is closed by a twist-off cap 42. A first face side of tubular porous substrate 9 engages a tubular projection 43 formed at an inner side of cap 42. A cover 44 is rotatably connected to cap 42 within projection 43, so as to press substrate 9 against an annular web 39 of can 41, so that an elastic O-ring 45 is sealingly compressed between impermeable layer 37 of substrate 9 and web 39. Since cap 42 can be screwed on and off without imparting any torque upon substrate 9, there is no risk of bending or breaking capillary tube 13 extending from port 3 into recess 11 of substrate 9.

Figure 13:
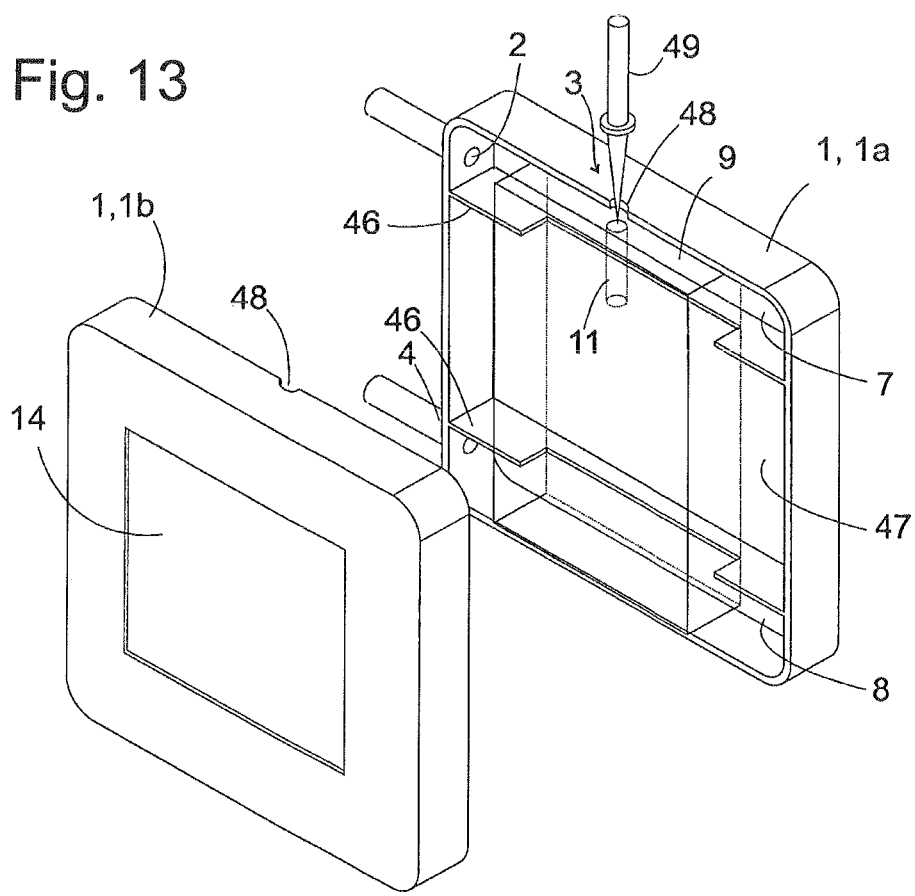
FIG. 13 is an exploded view of a culture vessel according to a fifth embodiment of the invention.

FIG. 13 is an exploded view of a cell culture system according to a fifth embodiment of the invention. Here the culture vessel has a substantially cuboid shape and comprises two flat shells 1a, 1b. As shown in FIG. 14, an inner cavity of shell 1a is subdivided by two horizontal walls 46. Both walls 46 have a cutout in which cuboid porous substrate 9 is tightly received. Similar horizontal walls, not shown, are formed in shell 1b, so that when the two shells are welded or glued together at their edges with the substrate 9 in between, the walls 46 combine to divide the internal cavity of vessel 1 into a first space 7 at the top, communicating with port 2, a second space 8 at the bottom, communicating with port 4, and a third space 47 in between. Cutouts 48 of shells 1a, 1b combine to form port 3. A short tube 49 installed at port 3 has a capillary tip which will engage recess 11 in substrate 9. A semi-permeable diaphragm 14 formed in shell 1b enables gases to be exchanged between third space 47 and the atmosphere outside vessel 1.

In operation, a culture medium is supplied by port 2 and is absorbed in substrate 9 by capillary action. After passing through the substrate 9, the culture medium drips freely off a bottom side of substrate 9 in space 8 and is withdrawn through port 4. Within the third space 47, a lateral surface of substrate 9 is exposed to an atmosphere formed by gases that have passed through diaphragm 14.

| Reference numerals | |
|---|---|
| 1 | cell culture vessel |
| 2 | port |

-continued

| Reference numerals | |
|---|---|
| 3 | port |
| 4 | port |
| 5 | tubular projection |
| 6 | cavity |
| 7 | first space |
| 8 | second space |
| 9 | porous substrate |
| 10 | edge |
| 11 | recess |
| 12 | center |
| 13 | capillary tube |
| 14 | diaphragm |
| 15 | porous body |
| 16 | forth port |
| 17 | chamber |
| 18 | gap |
| 19 | cutout |
| 20 | edge |
| 21 | circumferential wall |
| 22 | step |
| 23 | spacer ring |
| 24 | cutout |
| 25 | rubber membrane |
| 26 | syringe |
| 27 | injection needle |
| 28 | clamp |
| 29 | flange |
| 30 | spacer ring |
| 31 | KF support ring |
| 32 | O-ring |
| 33 | internal cavity |
| 34 | part of space 8 |
| 35 | spacer web |
| 36 | cover |
| 37 | impermeable layer |
| 38 | platelet |
| 39 | web |
| 40 | point |
| 41 | can |
| 42 | cap |
| 43 | projection |
| 44 | cover |
| 45 | O-ring |
| 46 | wall |
| 47 | third space |
| 48 | cutout |
| 49 | tube |

The invention claimed is:

1. A cell culture system for fermentation or cultivation of at least one of cells, tissues or tissue cell cultures, organs or organ cell cultures and multicellular organisms, comprising:
    a system vessel in which at least one cavity is formed;
    a first, a second and a third port formed in the cavity;
    at least one porous substrate installed within the cavity, wherein the porous substrate is configured to allow fluid flowing from any one of the first, the second and the third ports to pass through the porous substrate to any other of the first, the second and the third ports; and,
    at least one channel extending from a first one of the first port, the second port and the third port into and within the porous substrate and towards an inner region of the porous substrate,
    said channel extending towards the geometrical center of the porous substrate, thus allowing an inoculum to flow freely towards the center of the porous substrate.

2. The cell culture system of claim 1, wherein the porous substrate forms a partition between upstream and downstream portions of the cavity, wherein a second one of the first, the second and the third ports is connected to an upstream portion, and wherein a third one of the ports is connected to a downstream portion.

3. The cell culture system of claim 1, wherein the porous substrate is of a cubic, discoid, tubular or cylindrical geometry.

4. The cell culture system of claim 1, wherein the porous substrate has edges in sealing contact with walls of the cavity.

5. The cell culture system of claim 2, wherein the porous substrate comprises a tube, wherein one of the upstream and downstream portions comprises a portion extending within the tube, and wherein the other of the upstream and downstream portions comprises a portion extending around the tube.

6. The cell culture system of claim 1, wherein the at least one channel is a recess formed in the porous substrate or a gap between two parts of the porous substrate or a tube extending into the substrate.

7. The cell culture system of claim 4, wherein at least part of the walls of the cavity is gas-permeable.

8. The cell culture system of claim 1, wherein a porosity and surface properties of the porous substrate allow water to rise within the porous substrate by capillary force.

9. The cell culture system of claim 1, wherein a fraction of at least 50% of a total pore volume of the porous substrate is formed by pores the size of which differs by a factor of not more than 2.

10. The cell culture system of claim 9, wherein a minimum pore size of the fraction of the total pore volume is 10 μm or the maximum pore size of said majority of pores is 500 μm.

11. The cell culture system of claim 1, wherein a porosity of the porous substrate is in a range from 15% up to 90%.

12. The cell culture system of claim 1, wherein the system vessel comprises at least one additional port for temporary or permanent insertion of probes or sensors for measuring physical and chemical parameters like, but not limited to, pH, temperature, concentration of oxygen, carbon dioxide, glucose and lactate.

13. A method of operating the cell culture system of claim 1, comprising the steps of
    a) introducing cells to be cultivated into the porous substrate by said channel,
    b) feeding a culture medium by a second one (2) of said ports,
    c) discharging the culture medium by a third one (4) of said ports.

14. The method of claim 13, wherein step a) is carried out while no culture medium is fed by said second port (2).

15. The method of claim 13, wherein in step a) the cells are introduced within a volume of inoculum which is smaller than the volume of the pores of the porous substrate (9).

16. The cell culture system of claim 9, wherein the fraction of the total pore volume of the porous substrate formed by pores the size of which differs by a factor of not more than 2, is at least 60%.

17. The cell culture system of claim 9, wherein the fraction of the total pore volume of the porous substrate formed by pores the size of which differs by a factor of not more than 2, is at least 75%.

18. The cell culture system of claim 9, wherein a minimum pore size of the fraction of the total pore volume is 10 μm and the maximum pore size of said majority of pores is 500 μm.

19. The cell culture system of claim 1, wherein a porosity of the porous substrate is in a range from 25% up to 60%.

20. The cell culture system of claim 1, wherein the porous substrate is formed from a material selected from the group consisting of: polycarbonate, carbon, ceramic and borosilicate glass.

* * * * *